US005679310A

United States Patent [19]

Manns

[11] Patent Number: 5,679,310

[45] Date of Patent: Oct. 21, 1997

[54] HIGH SURFACE AREA MULTIWELL TEST PLATE

[75] Inventor: Roy L. Manns, Marshfield Hills, Mass.

[73] Assignee: Polyfiltronics, Inc., Rockland, Mass.

[21] Appl. No.: 501,204

[22] Filed: Jul. 11, 1995

[51] Int. Cl.[6] .............................. C12M 1/12; C12M 1/20

[52] U.S. Cl. .................... 422/102; 435/288.4; 435/297.5

[58] Field of Search .................................. 422/101–102; 435/288.4, 288.5, 297.5

[56] References Cited

U.S. PATENT DOCUMENTS

| | | | |
|---|---|---|---|
| 4,652,533 | 3/1987 | Jolley | 436/578 |
| 5,047,215 | 9/1991 | Manns | 422/101 |
| 5,382,512 | 1/1995 | Smethers et al. | 435/6 |

*Primary Examiner*—Lyle A. Alexander
*Attorney, Agent, or Firm*—Lappin & Kusmer LLP

[57] ABSTRACT

The present invention comprises a microtiter plate formed of a substantially rigid, polymeric plate having a substantially flat upper surface and a regular array of similar wells, typically either cylindrical or frusto-conical, each well being defined by a fluid-impervious peripheral wall extending a predetermined distance along an axis substantially perpendicularly to that upper surface between an opening in the upper surface and a well bottom. Disposed within the well adjacent the bottom is a porous structure providing a surface area at least five times greater than the surface area of the interior well bottom. The well bottom may be either fluid impervious or pervious. Where the well bottom is fluid pervious, it may be formed from a fluid impervious sheet apertured to accept and be bonded to the peripheries of the ends of a plurality of fluid pervious ultrafiltration fibers that may have hollow cores. In embodiments with fluid pervious well bottoms, a vacuum plenum is provided below the wells for drawing fluid from the wells through the pervious material. In embodiments in which the well bottom is fluid impervious, the porous structure within the well and coupled to the inner surface of the well bottom can be formed from either continuous or closed cells, a plurality of loops of fibers having both ends coupled to the bottom, a plurality of fibers having one end coupled to the bottom, a coil of fiber, and other configurations.

16 Claims, 3 Drawing Sheets

HIGH SURFACE AREA MULTIWELL TEST PLATE

This invention relates to biological, chemical and biochemical assays, and particularly to multiwell sampling and filtration devices useful in such assays.

BACKGROUND OF THE INVENTION

Multiwell test plates used for isotopic and nonisotopic in-vitro assays are well known in the art and are exemplified, for example, by those described in U.S. Pat. Nos. 3,111,489, 3,540,856, 3,540,857, 3,540,858, 4,304,865, in U.K. Patent 2,000,694 and in European Patent Application 0,098,534. Typically, such test plates have been standardized in the form of the so-called microtitre plate that provides ninety-six depressions or cylindrical wells of about 0.66 cm in diameter and 1.3 cm deep, arranged in a 12×8 regular rectangular array, spaced about 0.9 cm. center to center. A recent form of another multiwell test plate employs the same footprint as the ninety-six well plate but provides 384 wells arranged as four blocks of ninety-six wells each, the wells, of course, being much lesser in diameter than those of the ninety-six well plate.

Selected wells in such a test-plate are typically used to incubate respective microcultures, followed by further processing to harvest the incubated material. Each well typically may include a filtration element so that, upon application of a vacuum or air pressure to one side of the plate, fluid in each well is expressed through the filter, leaving solids, such as bacteria and the like, entrapped in the well. In typical use, specimens from up to ninety-six different individuals may be respectively inserted in corresponding wells in a plate in the course of an assay, the specimens typically all being inserted prior to filtration and completion of the assay. Such procedures are generally used both for clinical diagnostic assays and to screen a large number of specimens, for example, drugs in pharmaceutical research. For some application, the bottom of the wells are not porous, but are fluid-impervious, the interior walls and/or bottom of the well being coated with a specific reactant such as an enzyme, antibody or the like.

It has been common practice to manufacture such plates as a multi-layer structure that may include one or more layers of filter membrane disposed to cover the bottom apertures of all the wells, the filtration sheet being bonded to the periphery of one or more of the well apertures. Unfortunately, such structure may permit fluid expressed through the filter medium from one well, as by capillary action, gravity or application of pressure, to wick through adjoining portions of the filter medium to the filter medium covering an adjacent cell aperture. This mingling of fluids in the filter medium from adjacent wells is known as "cross talk" and is considered highly undesirable inasmuch as it can serve as a source of contamination, interfere with an assay, and cause ambiguity and confusion in interpreting assay results. Of course, where the well walls and/or bottom are not fluid pervious, the issue of cross talk due to wicking is non-existent. Additionally, the pore structure of such filter sheets or membranes is generally not much below 0.001 μm so is capable of trapping only fairly large molecular structures.

U.S. Pat. No. 5,047,215 discloses a micro-titre test plate in which cross-talk is minimized or eliminated by ultrasonically bonding the bottom edges of the wells in a flat incubation tray with the peripheral upstanding edges of holes in a parallel substantially rigid harvester tray, a sheet of filter paper having been trapped between the two trays and incorporated into the fused edges of the respective wells and holes during thermal bonding. In such a structure, typical of microtiter plates, the surface area available for coating with a reagent or reactant is limited to walls and bottom of the well in the incubation tray, and dilute samples of material reactive with the reagent or reactant may afford so little product as to be detectable with great difficulty.

OBJECTS OF THE INVENTION

A principal object of the present invention is to therefore provide multi-well, multi-layer test plates in which the reactive surface area is substantially increased. Other objects of the present invention are to provide such a test plate incorporating filter elements, in which the cross-talk problem has been overcome; to provide a method of making such test plates, and to provide several embodiments of such test plates in which the reactive surface area provided within each well has been substantially increased.

SUMMARY OF THE INVENTION

To these ends the present invention comprises a multiwell test plate that includes a substantially rigid, polymeric tray having a substantially flat upper surface and a regular array of similar wells, typically cylindrical or frusto-conical, each well being defined by a fluid-impervious peripheral wall extending a predetermined distance along an axis substantially perpendicularly to the upper surface between an opening in that surface and a well bottom. Disposed within the well adjacent the bottom is means for defining a surface area substantially greater than the surface area of the interior well bottom. The well bottom may be either fluid impervious or pervious.

In embodiments where the well bottom is fluid pervious, it may be formed from a fluid impervious sheet having a plurality of small apertures that accept and are bonded to the peripheries of the ends of one or more open cell, porous elements, for example a plurality of fluid-pervious ultrafiltration fibers that may have hollow cores. Regardless of the form of the porous elements, the latter provide the necessary means for defining the increased surface area for the cell bottom. In embodiments with fluid pervious well bottoms, a vacuum plenum is preferably utilized below the wells for drawing fluid from the wells through the pervious material.

In embodiments in which the well bottom is fluid impervious, the requisite means for defining the increased surface area can be simply a sheet or membrane of highly porous material either open or closed cell, or a plurality or bundle of elongated elements, disposed in and coupled at the bottom of each well, the combined surface area of the membrane or bundle, in each well, being substantially greater than the surface area of a comparable flat bottom for such well.

In one specific embodiment, the bottom of each well is formed, typically as a generally flat surface of the usual 0.2 $cm^2$, perforated with a plurality of small apertures. Disposed in each such aperture are at least one of each of the ends of the elongated elements of the bundle, the elements being provided in forms such as tapes, fibers, sheets and combination thereof, such ends being sealed within each such aperture to provide a liquid impervious joint. In another version of such embodiment, each elongated element is a microporous, hollow fiber, typically polymeric, formed into an upstanding loop or loops having the peripheries of its ends sealed within a corresponding pair of apertures in the well bottom. In yet another version of such embodiment, the elongated elements are microporous, hollow fibers having the periphery of one end sealed within a corresponding aperture, the other end of the fibers extending from the seal into the well interior being provided with blind terminations. In still another version of such embodiment, the surfaces of the elongated elements are fluid impervious, whether formed as loops or straight segments.

In yet another embodiment of the present invention, each well is formed with a substantially conical bottom having a truncated apical aperture, i.e. frusto-conical. Sealed within that aperture is a bundle of ends of elongated elements extending upwardly into the well, such elements being either porous or imporous and formed as either loops or substantially linear elements.

These and other objects of the present invention will in part be obvious and will in part appear hereinafter. The invention accordingly comprises the apparatus possessing the construction and arrangement of parts exemplified in the following detailed disclosure, and the method comprising the several steps and the relation and order of one or more of such steps with respect to the others, the scope of the application of which will be indicated in the claims.

For a fuller understanding of the nature and objects of the present invention, reference should be had to the following detailed description taken in connection with the drawings wherein line numerals denote like parts.

DETAILED DESCRIPTION

Multiwell test plate 20 of the present invention comprises a rectangular body having a preferably substantially planar top surface 22, plate 20 being formed of a substantially rigid, water-insoluble, fluid-impervious, typically thermoplastic material substantially chemically non-reactive with the fluids to be employed in the assays to be carried out with the plate. The term "substantially rigid" as used herein is intended to mean that the material will resist deformation or warping under a light mechanical or thermal load, which deformation would prevent maintenance of surface 22 as substantially planar, although the material may be somewhat elastic. Suitable materials are polyvinyl chloride with or without copolymers, polyethylenes, polystyrenes, polystyrene-acrylonitrile, polypropylene, polyvinylidine chloride, and the like. Polystyrene is a preferred material, inasmuch as it characterized by very low, non-specific protein binding, making it specially suitable for use with samples, such as blood, viruses and bacteria, incorporating one or more proteins of interest.

Figure 1:
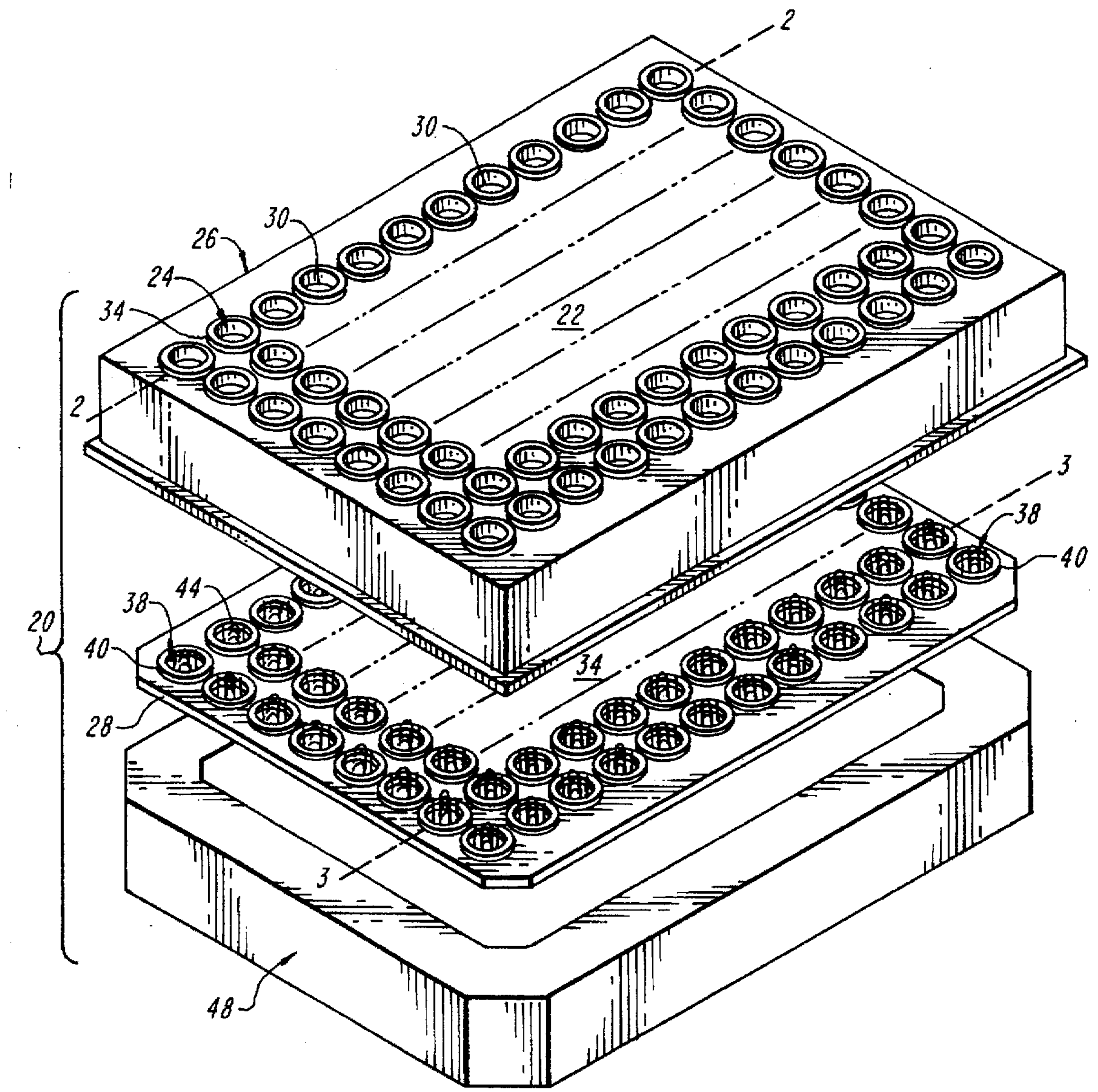
FIG. 1 is an exploded isometric view of one embodiment of multi-well filter apparatus incorporating the principles of the present invention.

As shown in FIG. 1, plate 20 is provided with a plurality (typically ninety-six) of identical wells 24. Although wells 24 can be formed integrally, as by injection or blow molding for example, a preferred method of manufacture is to form plate 20 from upper tray 26 which defines the upper portion of each well and lower or bottom tray 28 which defines at least the bottom of each well. The well depth, together with the diameter of the well, determines the volume of liquid that the well can hold. Typically for example, each well in a ninety six well plate is about 0.66 cm. in diameter and 1.3 cm. deep, and the wells are preferably arranged in a 12×8 regular rectangular array spaced about 0.9 cm. center-to-center. As will be delineated further herein, the wells may be cylindrical, conical or have other configurations depending upon the wishes of the designer or user.

Figure 2:
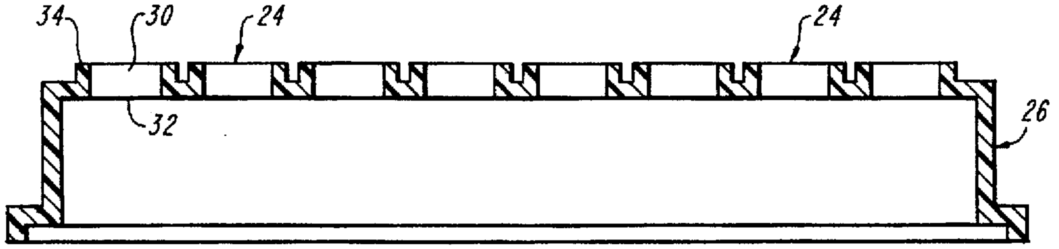
FIG. 2 is an enlarged cross-sectional view, taken along the line 2—2 of the upper tray of the embodiment of FIG. 1.

As shown particularly in FIG. 1–6 inclusive, each of wells 24 extends, along a respective axis A—A disposed substantially perpendicularly to the plane of surface 22, from a respective aperture 30, typically circular in cross section, provided in planar surface 22 in plate 20. Each of wells 24 has a corresponding opening 32 at the opposite end thereof from its respective aperture 30. Preferably, each well 24 is formed, as shown in FIG. 2, by integrally molding it in part from upper tray 26, to form fluid-impervious peripheral wall 34, preferably extending upwardly from surface 22 to form a rim or lip around its respective aperture 30.

Figure 3:
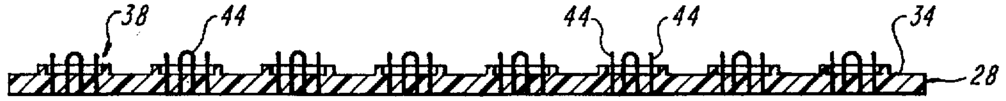
FIG. 3 is an enlarged cross-sectional view, taken along the line 3—3 of the bottom tray of the embodiment of FIG. 1.

Plate 20 includes bottom tray 28, shown in FIGS. 1 and 3 as a rectangular slab or sheet defining at least one substantially planar surface 34. A plurality of well bottoms or closure elements 38 are formed in bottom tray 28, as shown in FIG. 3, by molding or other known techniques, in an array disposed in the same configuration as openings 30. Each closure element 38 is shaped and dimensioned in cross-section so as to register with a corresponding one of openings 32 when sheet 36 and the underside of tray 26 abut with the planes of surfaces 22 and 32 parallel to one another. As shown particularly in FIG. 3, typically each closure element 38 is provided with an upstanding lip or rim 40. The external dimension of rim 40, such as the diameter, is sufficiently larger than the internal dimension, such as the diameter, of well wall 34 so that each wall 34 can fit snugly around the external periphery of the corresponding rim 40 and can be sealed readily to the latter as by adhesives, thermal bonding and the like, thereby fully forming each of wells 24. It will be seen that each well 24 thus extends a predetermined distance along an axis A—A substantially perpendicularly between opening 32 surface to well bottom 38.

Figure 5:
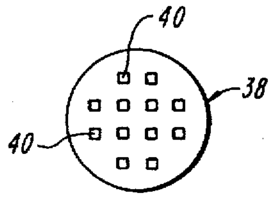
FIG. 5 is a plan view of the underneath surface of one of the well bottoms defined by the bottom tray shown in FIG. 3
Figure 4:
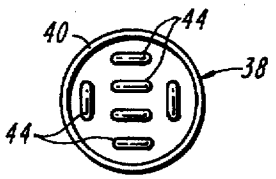
FIG. 4 is a plan view of the upper surface of one of the well bottoms defined by the bottom tray shown in FIG. 3

As illustrated in the embodiment shown in FIG. 5, each closure element 38 includes an even plurality (for example, twelve) of small perforations 40 through tray 28 typically arrayed as two crossed parallel double rows. A large number of different arrays of such perforations can be readily designed. As shown particularly in FIGS. 3 and 6, disposed in each pair of such perforation 40 are respective ends 42 of one of elongated elements 44 of a bundle, thus forming loop 45 extending upwardly from surface 32 into the interior of the corresponding well 24. In the case where closure element 38 includes twelve perforations as described above, it will be apparent that loading those perforations with corresponding ends 42 will result in an array of six loops 45, four of which are parallel with one another, the other two loops being perpendicular to the array of four loops. In the embodiment shown in FIG. 6, elements 44 may be provided in forms such as tapes, fibers, sheets and combination thereof, in a plurality that is one-half of the number of perforations. Where, for example, each closure element 34 is formed with twelve perforations, elements 44 would be six in number to provide the requisite twelve ends. Elements 44 can be inserted by hand or by machine, and, for example, where elements 44 are emplaced by a tufting machine through an unapertured bottom tray 38, it will be apparent that the tufting machine will simultaneously perforate the sheet and insert the requisite element. Each of ends 42 is sealed, by thermal bonding, solvent bonding, adhesives or the like, within each corresponding perforation so as to provide a liquid impervious joint between the internal periphery of the perforation and the external periphery of the respective end 42 of element 44, while providing a path for fluid communication between the inside and outside of the well through the bottom of the latter.

Figure 6:
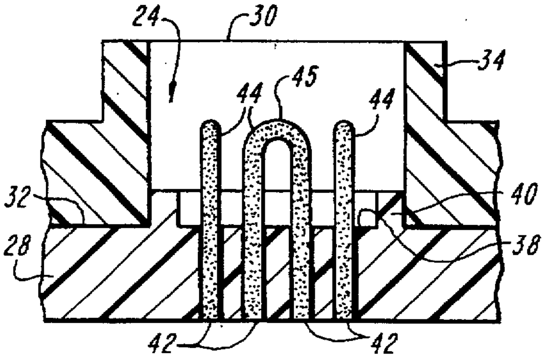
FIG. 6 is an enlarged fragmentary cross-sectional view of a single cylindrical well formed by bonding the trays of FIGS. 2 and 3.

It will be seen that thus, emplaced in each well 24 is a plurality or bundle of elongated elements 44, the combined surface area of which, in each well, is substantially greater than the surface area of a comparable flat bottom for such well. In the embodiment of FIG. 6, in which wells 24 are substantially cylindrical in shape, the elongated elements are microporous, hollow fibers, typically polymeric. One advantage of this embodiment of the present invention is that it makes use of commercially available hollow, porous fibers. The filtration provided by such fibers is known at ultrafiltration in that the average pore size is below 0.001 μm and hence is indicated in terms of "molecular weight cutoff" (MWC) which expresses numerically the molecular weight of the smallest molecule the filter will retain. A wide range of such fibers are available commercially, from below 5K Dalton in discreet increments to 1 mil K Dalton, from such polymers as polysulphone, polypropylene, cellulose acetate and the like. This confers a distinct advantage on the present invention in that such fibers are available with MCWs as low as 1000, a particle size that commercially available membranes, conventionally used to serve as filters for wells in microtiter plates, cannot filter.

Figure 7:
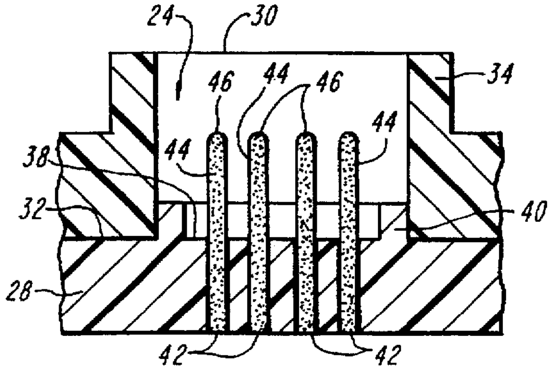
FIG. 7 is an enlarged fragmentary cross-sectional view of another embodiment showing other elongated elements emplaced in a closure element in a well configuration similar to that of FIG. 6.

In the embodiment illustrated in FIG. 7, elongated elements 44, also preferably in the form of microporous, hollow fibers, are emplaced in closure element 38 in a configuration that differs from that shown in FIG. 6 in that the periphery of only one end 42 of each of elements 44 are sealed within apertures 40, the other end 46 extending upwardly into the interior of corresponding well 24. In such case, ends 46 are preferably blind in that any internal hollow cores or canals are closed at ends 46. Although it is expected that commercially available fibers will usually have a circular cross-section, the cross-sectional configuration of elements 44 can be quite arbitrarily chosen, the corresponding shape of apertures 40 being selected correspondingly.

It will be appreciated that in those embodiments employing filtration elements disposed to provide fluid communication through bottom tray 38 from the interior of wells 24 to outside of those wells, it is preferable to provide a closed hollow chamber or plenum 48 disposed below tray 28 to apply reduced pressure or vacuum to those filtration elements. In such case, the hollow interior of plenum 48 is pneumatically connectable to an external vacuum source through a hosecock (not shown) extending through a wall of the plenum.

The principles of the present invention can also be embodied in test plates in which the well bottoms do not filter but are fluid impervious instead. For example, in the embodiment shown in FIG. 8, a plurality of elongated elements 50 such as fibers, yarns, sticks, strips and the like are embedded in only the portion of tray 28 adjacent surface 32 within well 24 to extend substantially upwardly inside well 24. In such case, because tray 28 is formed as an imperforate sheet of a fluid impervious material, there can be no fluid communication between the interior of the well and the underside of tray 28, and the possibility of fluid cross-talk between wells in a test plate is eliminated. A plurality of imporous elements 50, as shown, collectively contribute a much greater surface area than would be available without such elements. If, however, one provides elements 50 in porous form, the available reactive surface area within the well will be increased far beyond that provided by solid imporous elements 50. The use of solid elements 50 minimizes, however, retention of fluid on the increased reactive surface that would otherwise tend to occur with porous elements 50, and may, in some cases, be preferable.

Figure 9:
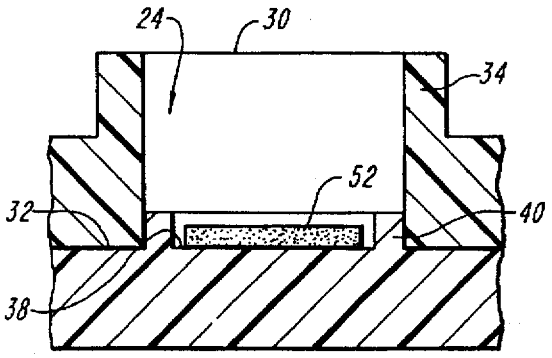
FIG. 9 is an enlarged fragmentary cross-sectional view of a fragment of yet another embodiment of the well similar to that of FIG. 6.
Figure 10:
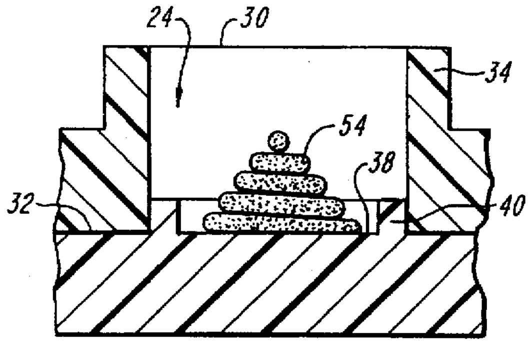
FIG. 10 is a fragmentary enlarged cross-sectional view of still another embodiment of the well similar to that of FIG. 6.

Alternatively where it is desired to increase the surface area within the well by using a porous material, as shown in FIG. 9 the bottom of well 24 can be formed by simply providing tray 28 with closure elements having a smooth, flat surface 32 portion within rim 40. Disposed on that flat surface portion is a porous membrane 52 which may be bonded to surface 32 if desired, as by any of many known techniques. The surface area available can be increased over a simple porous membrane by forming the requisite means for defining an increased surface from a single highly elongated microporous fiber arranged as spiral or coil 54 which preferably is in conical form with its apex facing upwardly within well 24, as shown in FIG. 10. Such configuration provides the desired high surface area in a form readily viewable through opening 30.

Figure 8:
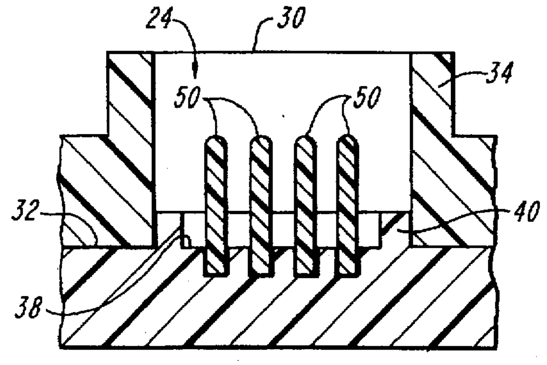
FIG. 8 is an enlarged fragmentary cross-sectional view of alternative embodiment to the well similar to that of FIG. 6.
Figure 11:
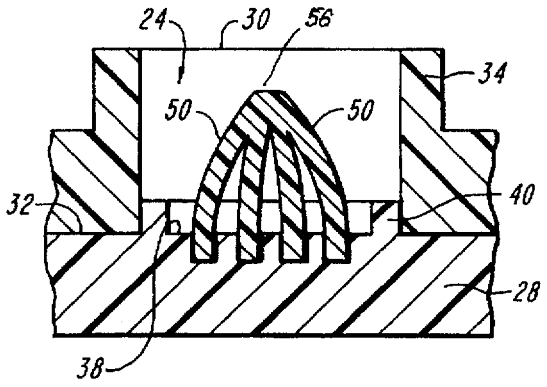
FIG. 11 is an enlarged fragmentary cross-sectional view of a fragment of yet another embodiment of the well similar to that of FIG. 8.

A variation of the structure of FIG. 8 is shown in FIG. 11 wherein one end of each of the plurality of elongated elements 50 is embedded in only the portion of tray 28 adjacent surface 32 within well 24 to extend substantially upwardly inside well 24 and the other ends of elements 50 are coupled, as by fusing, to one another to form a crown 56. Thus elements 50 are gathered together in a bundle and can be more readily emplaced in the well bottom, as by mechanical handling equipment.

Figure 12:
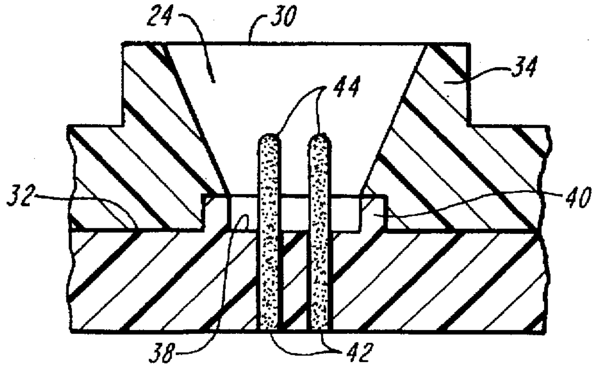
FIG. 12 is an enlarged cross-sectional view of still another embodiment of a well embodying the principles of the present invention in a frusto-conical well shown in fragment.

As indicated above, it may be desirable to form the wells in the test plate of the invention in other than cylindrical form. In the alternative configuration shown in FIG. 12, each well 24 is provided as an inverted, substantially frustoconical depression in tray 34, i.e. the well is characterized as having a circular cross-section that decreases as a function of the depth, at least to a level adjacent a substantially flat, circular bottom provided by one of closure elements 38 in tray 28. As shown in FIG. 12, the well bottom can be apertured as earlier described herein and therefore fluid permeable. In the embodiment shown, a plurality of the apertures being sealed to the peripheries of one end of each of a like plurality of microporous elements 44 in a manner similar to that shown in FIG. 7. In other embodiments, well 24 can include other various means for defining an increased surface area as described above in connection with yet other embodiments of the present invention. Alternatively, the well bottom facing the frustum of the conical shape of the well can be fluid impermeable, and means for defining an increased surface area emplaced thereon as also earlier described in connections with other embodiments of the present invention incorporating fluid impermeable bottoms.

Since certain changes may be made in the above apparatus and process without departing from the scope of the invention herein involved, it is intended that all matter contained in the above description or shown in the accompanying drawing shall be interpreted in an illustrative and not in a limiting sense.

What is claimed is:

1. In a microtiter plate comprising a substantially rigid plate having at least one substantially flat surface and at least one well therein, said well being defined by an opening in said surface, a substantially fluid-impervious barrier forming a bottom of said well and spaced apart from and extending substantially parallel to said surface, and a fluid-impervious peripheral wall extending a predetermined distance along an axis substantially perpendicularly to said surface between said opening in said surface and said well bottom, the improvement comprising means bonded to said well bottom and extending, at least in part, upwardly within said well from said well bottom toward said flat surface, for defining a surface area substantially greater than the cross-sectional area of said well adjacent said well bottom and orthogonal to said axis.

2. A microtiter plate as defined in claim 1, wherein said plate includes a plurality of said wells arranged in a regular array.

3. A microtiter plate as defined in claim 2, wherein the dimensions of said wells are the same.

4. A microtiter plate as defined in claim 3, wherein said wells are substantially cylindrical.

5. A microtiter plate as defined in claim 3, wherein said wells are substantially frusto-conical.

6. A microtiter plate as defined in claim 1, wherein said well bottom includes at least one aperture therethrough, and said plate includes porous material that is fluid pervious and extends through said aperture in said well bottom so as to provide fluid communication through said material from the interior of said well through said well bottom to outside said well.

7. A microtiter plate as defined in claim 6, wherein the average pore size in said porous material is below about 0.001 μm.

8. A microtiter plate as defined in claim 6 including means coupled to the underside of said well for applying reduced gas pressure to the underside of said well bottom.

9. A microtiter plate as defined in claim 6, wherein said porous material comprises a membrane.

10. A microtiter plate as defined in claim 6, wherein said porous material comprises at least one porous fiber.

11. A microtiter plate as defined in claim 10, wherein said porous fiber has a hollow core.

12. A microtiter plate as defined in claim 10, wherein the peripheries of the ends of said porous fiber are bonded to the corresponding inner peripheries of respective apertures in said well bottom so as to provide said fluid communication.

13. A microtiter plate as defined in claim 10 including a plurality of said porous fibers, the respective ends of said fibers being bonded to corresponding inner peripheries of respective apertures in said well bottom.

14. A microtiter plate as defined in claim 10 including a plurality of said porous fibers, only one end of each of said fibers being bonded to corresponding inner peripheries of a respective aperture in said well bottom so as to provide said fluid communication.

15. A microtiter plate as defined in claim 10, wherein both ends of at least some of said fibers are respectively bonded to said well bottom so said fibers form loops extend upwardly from said bottom into the interior of said well.

16. A microtiter plate as defined in claim 10, wherein said means for defining comprises at least one porous fiber arranged substantially in a conical coil within said well.

* * * * *

Disclaimer 5,679,310—Roy L. Manns, Marshfield Hills, Mass. HIGH SURFACE AREA MULTIWELL TEST PLATE. Patent dated October 21, 1997. Disclaimer filed March 24, 1998, by the assignee, Whatman International Limited.

Hereby enters this disclaimer to claim 7 of said patent.

(*Official Gazette,* June 2, 1998)